United States Patent [19]

Bohn

[11] 4,041,021

[45] Aug. 9, 1977

[54] AP-GLYCOPROTEINS AND PROCESS FOR ISOLATING THEM

[75] Inventor: Hans Bohn, Marbach near Marburg an der Lahn, Germany

[73] Assignee: Behringwerke Aktiengesellschaft, Marburg an der Lahn, Germany

[21] Appl. No.: 592,179

[22] Filed: July 1, 1975

Related U.S. Application Data

[63] Continuation of Ser. No. 354,117, April 24, 1973, abandoned.

[30] Foreign Application Priority Data

Apr. 29, 1972 Germany .................... 2221261

[51] Int. Cl.² ............................................. C07G 7/00
[52] U.S. Cl. ............................ 260/112 B; 424/12
[58] Field of Search ................. 260/112 R, 112 B; 424/12

[56] References Cited

PUBLICATIONS

Chemical Abstracts, vol. 78, No. 5609w, Bohn, 1973.
Chem. Abs., vol. 76, No. 70559g, Bohn, 1971.
Chem. Abs., vol. 59, No. 9157a-b, Mansfield, 1963.
Chem. Abs., vol. 78, No. 55867d 55868e Hofmann & Straube, 1972.
Chem. Abs., vol. 78, No. 95495n, Bohn, 1972.
Chem. Abs., vol. 67, No. 114847v, Sotnikova, 1967.
Chem. Abs., vol. 66, No. 9561d, Bundschuh, 1966.
Chem. Abs., vol. 61, No. 4695f, Hansen, 1964.
Chem. Abs., vol. 51, No. 16804e-g, Centonze, 1957.
Chem. Abs., vol. 55, No. 23724g-i, 23725a Centonze, 1957.
Chem. Abs., vol. 76, No. 32096w, Bohn, 1971.
Boenisch, "Biochimica et Biophysica Acta, 214, 1970, pp. 135-140.
Schmid, "J. Am. Chem. Soc.", vol. 77, 1955, pp. 742-745.
Bezkorovainy, "Biochimica et Biophysica Acta", 49, 1961, pp. 559-565.
Bezkorovainy, 37 Dissertation Abstracts", 1962, pp. 2567-2568.
Gottschalk, "Glycoproteins", Elsevier Pub., New York, 1966, pp. 362-367 & 561.

*Primary Examiner*—Paul R. Michl
*Attorney, Agent, or Firm*—Curtis, Morris & Safford

[57] ABSTRACT

The invention relates to two new glycoproteins called AP-glycoproteins, in particular the $\beta_1$-AP-glycoprotein which is characterized by an electrophoretic migration speed in agar gel in the range of that of the $\beta_1$-globulins and a molecular weight of about 100,00 ($\pm$ 10%) and the alpha$_2$-AP-glycprotein which is characterized by an electrophoretic migration speed in agar gel in the range of that of the alpha$_2$- glycoproteins and a molecular weight of about 300,000 ($\pm$ 10%), as well as to their use as reagents and for the preparation of anti-serums.

5 Claims, No Drawings

AP-GLYCOPROTEINS AND PROCESS FOR ISOLATING THEM

This is a continuation of application Ser. No. 354,117, filed Apr. 24, 1973 now abandoned.

The present invention relates to AP-glycoproteins and to a process for isolating them.

A process for isolating a pregnancy-specific $\beta_1$-glycoprotein has already been proposed. In this proposal, however, it has not been mentioned that during pregnancy two other glycoproteins are present which are not specific to pregnancy, since they are also found in the serum of patients affected by diseases of various geneses. Owing to this occurrence during pregnancy as well as during diseases, they are called AP-glycoproteins (AP = acute phase).

Now, we have found that these two AP-glycoproteins can be isolated from placentas or the blood of pregnant female human beings.

Accordingly, these two glycoproteins are the object of the present invention, i.e. the $\beta_1$-AP-glycoprotein which is characterized by an electrophoretic migration speed in agar gel in the range of that of the $\beta_1$-globulins and a molecular weight of about 100,000 ($\pm$ 10%) and the alpha$_2$-AP-glycoprotein which is characterized by an electrophoretic migration speed in agar gel in the range of that of the alpha$_2$-glycoproteins and a molecular weight of about 300,000 ($\pm$10%).

The fact that the AP-glycoproteins have a higher content of carbohydrates is proved by the change of their electrophoretic motility upon treatment with neuraminidase. After separation of the neuraminic acid, the $\beta_1$-AP-glycoprotein shows the motility of a gamma-globulin and the $\alpha_2$-AP-glycoprotein the motility of a $\beta_1$-globulin.

Such a strong shift is in general found only with plasma-proteins which contain at least 2 - 6 % of neuraminic acid or 10 - 30 % of carbohydrates.

The migratin speed in a polyacrylamide gel (5.5% of acrylamide at pH 8.5 in a Tris/citrate/borate buffer, Z. Clin. Chem. 4, 58 (1966)) is 62 for the $\beta_1$-AP-glycoprotein and 32 for the $\alpha_2$-AP-glycoprotein, when taking the migration speed of human albumine as 100.

Another object of the invention is a process for isolating these two AP-glycoproteins, wherein placentas or the blood of pregnant female human beings is fractionated according to known methods.

For isolating the AP-glycoproteins, comminuted placentas are extracted with a physiologically tolerated weak salt solution, for example a sodium chloride solution. An inactive pre-precipitate is separated from the extract at a weakly acid pH-value with the aid of diaminoethoxyacridine lactate and then the two glycoproteins are precipitated in the alkaline range by precipitation with diaminoethoxyacridine lactate. For separating the pre-precipitate, it is of advantage to apply the diaminoethoxyacridine lactate, preferably in the form of an aqueous solution, in a quantity of 5 - 10 % by weight, referred to the protein content of the extract. For the main precipitation which is suitably effected in a pH-range of from 7.5 to 9.0, it is of advantage to apply the diaminoethoxyacridine lactate in a quantity of 10 - 30 % by weight, referred to the protein content of the extract. For further purification, gel filtration with cross-linked dextrane, for example Sephadex G-150, and/or preparative zone electrophoresis may be applied.

After dialysis against a weak, for example 0.01 molar, Tris/hydrochloric acid buffer solution of pH 7.5 to 8.5, preferably 8.0, gel filtration is effected on cross-linked dextrane such as Sephadex G-150. For elution, there may be used, for example 0.1-molar Tris/hydrochloric acid buffer having a pH of 8.0 and containing 1 mole per liter of sodium chloride. In this elution process first the alpha$_2$-AP-glycoprotein is eluted, whereas the $\beta_1$-AP-glycoprotein leaves the column later on. The alpha$_2$-AP-glycoprotein is eluted immediately after the alpha-2-macro-globulin and the $\beta_1$-AP-glycoprotein is eluted immediately after the 7 S-gammaglobulin.

Both proteins are precipitated with the aid of ammonium sulfate (about 2 - 2.5 mole/l). After dissolution of the precipitates in distilled water, the solutions are dialyzed against a buffer solution such as ammonium bicarbonate having a pH-value of 8.0 to 8.5 and then further separated suitably in the same buffer by zone electrophoresis. The corresponding zones in the alpha$_2$ and $\beta_1$-range, respectively are eluted with ammonium bicarbonate and freeze-dried.

In order to isolate the two AP-glycoproteins from serum, the products of the invention are precipitated in the alkaline pH-range (pH 8 - 9) with diaminoethoxyacridine lactate from retroplacental serum. The acridine complex is combined with a sodium chloride solution, for example a 4 - 6, preferably 5 % solution, the precipitate that has formed is separated and rejected, and the supernatant is precipitated with the aid of solid ammonium sulfate (2 - 2.5 mol/l).

For separating the two AP-glycoproteins, gel-filtration may also be used, wherein the alpha$_2$-AP-glycoprotein is eluted after the alpha$_2$-macro-globulin and $\beta_1$-glycoprotein after the 7 S-gammaglobulin. Then, in the same manner as that described for the isolation from placentas, preparative zne electrophoresis is carried out. The molecular weights were determined on the ground of the behaviour during gel-filtration.

The AP-glycoproteins isolated according to the invention serve for the preparation of anti-serums. These anti-serums permit, with the aid of immunological methods (gel diffusion test, trans-migration electrophoresis, radio-immunological determination), to determine the state of a disease and to follow the course of diseases.

The immunological proof of the AP-glycoproteins is of importance for differential diagnosis, since there exist qualitative and quantitative differences in the occurrence of these proteins in different diseases. In addition, their immunological determination may be used for a control of the therapy. The proof is carried out with the serum of the patient.

The following Examples illustrate the invention:

EXAMPLE 1

Isolation from retroplacental serum 500 ml of retroplacental serum were diluted with 500 ml of distilled water and precipitated at pH 8.5 (0.1-N sodium chloride solution) with 350 ml of a 3 % diaminoethoxyacridine lactate solution. The precipitate was isolated by centrifugation and combined with 500 ml of a 5% sodium chloride solution, whereupon the acridine derivative precipitated. The acridine derivative that had precipitated was separated by centrifugation and the supernatant was precipitated by the addition of 30 g of solid ammonium sulfate per 100 ml. The precipitate so obtained cntained the two AP-glycoproteins. After having been dissolved in water, these proteins were separated by gel-filtration on Sephadex G-150 into fractions of 20 ml each (column 10 × 100 cm). For the elution, 0.1-molar Tris/hydrochloric acid buffer having a pH-value of 8.0 and contained 1.0 mole/l of sodium chloride was used. The fractions were tested with specific antiserums of rabbits (gel-diffusion test according to Ochterony).

The corresponding fractions in which the two products of the invention had been found were combined, precipitated with 30 g of ammonium sulfate per 100 ml of solution, dialyzed against a 0.075-molar ammonium bicarbonate solution and, for further purification, separated by preparative electrophoresis. For this purpose, polyvinyl chloride was used as the carrier and a 0.075 % ammonium bicarbonate solution was used as buffer.

The AP-glycoproteins were eluted from the corresponding zones, i.e. the $\beta_1$ and the alpha$_2$ range, respectively, of the globulins, with the same buffer and the eluates were subsequently lyophilized. During preparative electrophoresis, the alpha$_2$-AP-glycoprotein was found in the alpha$_2$-fraction and the beta$_1$-AP-glycoprotein in the beta$_1$-fraction.

EXAMPLE 2

Isolation from placentas 10 g of human placentas in deep-frozen state were comminuted and extracted with 10 liters of a 0.5 %-sodium chloride solution (1 hour at 5° – 10° C). 10 Liters of the extraction solution were adjusted to pH 6.0 with 20 % of acetic acid and at first combined with 1500 ml of a 3 % diaminoethoxyacridine lactate solution. The inactive pre-precipitate was separated by centrifugation and rejected. The supernatant was adjusted to pH 8.5 with the aid of 2N-sodium hydroxide solution and precipitated with 3 liters of the 3 % acridine salt solution. The precipitate, which contained the AP-glycoproteins, was separated with 6 liters of a 5% sodium chloride solution in the manner described in Example 1. After centrifugation, the supernatant was combined with 30% solid ammonium sulfate. The precipitate obtained upon filtration was dissolved in water and dialyzed against a 0.01-molar Tris/hydrochloric acid solution (pH 6.0). For removing gammaglobulin and hematoproteins, the solution was stirred with 150 g of wet carboxymethyl cellulose and then filtered. The AP-glycoproteins were isolated from the filtrate by precipitation with ammonium sulfate (30 % w/v). The precipitate was dissolved in water and separated as described in Example 1 by gel-filtration and preparative zone electrophoresis and purified. The yield was 15 mg of $\beta_1$-AP-glycoprotein and 5 mg of alpha$_2$-AP-glycoprotein.

We claim:

1. A process for isolating alpha$_2$-AP-glycoprotein and beta$_1$-AP-glycoprotein from a protein solution containing the same which comprises:
   a. adding diaminoethoxyacridine lactate to said protein solution at an alkaline pH in an amount from 10 to 30 percent by weight of the protein content of said solution, whereby a first precipitate forms;
   b. recovering said first precipitate and dispersing it in aqueous sodium chloride, whereby a second precipitate forms;
   c. separating and discarding said second precipitate and adding ammonium sulfate to the remaining supernatant liquid, whereby a third precipitate forms;
   d. separating said third precipitate and dissolving it in an aqueous solution;
   e. chromatographing said solution and collecting those fractions which contain the AP-glycoproteins;
   f. adding ammonium sulfate to said fractions in an amount from 2 to 2.5 mols per liter, whereby a further precipitate forms in every fraction;
   g. separating said further precipitates, dissolving them in water, and dialyzing the resulting solution against a buffer solution at a pH from 8.0 to 8.5;
   h. subjecting the dialyzed solutions to zone electrophoresis and recovering the zone in the alpha$_2$ range, which contains the alpha$_2$-AP-glycoprotein, and the zone in the beta$_1$ range, which contains the beta$_1$-AP-glycoprotein.

2. An isolated beta$_1$-AP-glycoprotein prepared by the process of claim 1, said glycoprotein having an electrophoretic migration speed in agar gel in the range of the beta$_1$-globulins and further having a molecular weight of about 100,000.

3. An isolated alpha$_2$-AP-glycoprotein prepared by the process of claim 1, said glycoprotein having an electrophoretic migration speed in agar gel in the range of the alpha$_2$-glycoproteins and further having a molecular weight of about 300,000.

4. A process as in claim 1 wherein said protein solution is retroplacental serum.

5. A process as in claim 1 wherein said protein solution is a placental extract.

* * * * *